United States Patent [19]

Sprunt et al.

[11] Patent Number: 5,069,065
[45] Date of Patent: Dec. 3, 1991

[54] METHOD FOR MEASURING WETTABILITY OF POROUS ROCK

[75] Inventors: Eve S. Sprunt, Farmers Branch; Samuel H. Collins, DeSoto, both of Tex.

[73] Assignee: Mobil Oil Corporation, Fairfax, Va.

[21] Appl. No.: 641,965

[22] Filed: Jan. 16, 1991

[51] Int. Cl.$^5$ ............................................. E21B 49/00
[52] U.S. Cl. .......................................... 73/153; 73/38
[58] Field of Search .................................. 73/153, 38

[56] References Cited

U.S. PATENT DOCUMENTS

| | | | |
|---|---|---|---|
| 2,794,338 | 6/1957 | Murphy et al. | 73/38 |
| 4,660,412 | 4/1987 | Gupta | 73/38 |
| 4,868,751 | 9/1989 | Dogru et al. | 364/422 |
| 4,907,448 | 3/1990 | Givens | 73/153 |
| 4,924,187 | 5/1990 | Sprunt et al. | 324/376 |
| 4,926,128 | 5/1990 | Givens | 324/376 |

OTHER PUBLICATIONS

Journal of Petroleum Technology, Nov. '86, "Wettability Literature Survey—Part 2: Wettability Measurement", pp. 1246–1262.
"Recommended Practice for Core-Analysis Procedure", API Recommended Practice 40 (RP 40), 1st Edition, Aug. 1960, pp. 2–55.

*Primary Examiner*—Jerry W. Myracle
*Attorney, Agent, or Firm*—Alexander J. McKillop; Charles J. Speciale; George W. Hager, Jr.

[57] ABSTRACT

A core sample of a porous rock having a wettability representative of a subterranean formation is saturated with a first medium. This first medium is then displaced with an immiscible second medium. Capillary pressure versus wetting phase saturation is measured during the displacement of the first medium with the second medium within the core sample. Mercury is injected into an evacuated core sample of the porous rock, mercury vapor acting as a wetting phase on the porous rock. Capillary pressure versus wetting phase saturation is measured during mercury injection on the evacuated core sample. The ratio of the two capillary pressure versus wetting phase saturation measurements is determined and taken to be an indicator of the wettability of different size pore throats in the porous rock.

11 Claims, 3 Drawing Sheets

METHOD FOR MEASURING WETTABILITY OF POROUS ROCK

BACKGROUND OF THE INVENTION

In the drilling of wells, such as oil or gas wells, core samples of porous rock are taken of the earth formation through which the wells are drilled and various characteristics of the rock are determined for the purpose of establishing different fluids in the formation, estimating the quantity of each fluid in the formation, the ease of flow through the formation, etc. Such core samples are also taken from producing reservoirs and characteristics of the rock are determined for the purpose of estimating particular fluid quantities, predicting production rates, etc. Particularly important among the characteristics of the porous rock commonly determined is wettability.

Many different methods of measuring wettability have been utilized, see "Wettability Literature Survey—Part 2: Wettability Measurement", *Journal of Petroleum Technology*, November 1986, pgs. 1246–1262, by William G Anderson. The quantitative wettability measurements include contact angles, imbibition and forced displacement, and USBM wettability method. Other wettability measurements include imbibition rates, microscope examination, flotation, glass slide method, relative permeability curves, permeability/saturation relationships, capillary pressure curves, capillarimetric method, displacement capillary pressure, reservoir logs, NMR and dye adsorption.

It is a specific object of the present invention to provide a new method for quantitatively measuring the degree of wettability of porous rock from a core sample taken from a subterranean formation as an indication of the formation's potential for oil or gas production.

SUMMARY OF THE INVENTION

In accordance with the present invention, a subterranean porous rock formation is investigated as to its wettability characteristic. More particularly, a core sample of a porous rock having a wettability representative of a subterranean formation is saturated with a first medium. Thereafter, the first medium is displaced with a second medium that is immiscible with the first medium. Capillary pressure versus wetting phase saturation is measured on the core sample during the displacement of the first medium with the second medium. Mercury is injected into an evacuated core sample of the porous rock. The mercury acts as a non-wetting phase on the porous rock while mercury vapor acts as a wetting phase on the porous rock. Capillary pressure versus wetting phase saturation is measured on the core sample during the mercury injection. The ratio as a function of wetting phase saturation of these two measurements of capillary pressure versus wetting phase saturations is taken to be an indicator of the wettability of different size pore throats in the porous rock.

In a more specific aspect, a first capillary pressure measurement $P_{cp}$ is conducted on the porous rock by saturating the core sample with a first medium and by then displacing the first medium with a second medium. A second capillary pressure measurement $P_{hg}$ is thereafter conducted on the porous rock by injecting mercury into an evacuated sample of the porous rock. In a mercury injection capillary pressure measurement, mercury saturation is measured as a function of mercury pressure.

$$P_{Hg} = \frac{2\,\sigma_{Hg} \cos\theta_{hg}}{RK} \quad (1)$$

where:
$\sigma_{Hg}$ is the interfacial tension of mercury.
$\theta_{hg}$ is the contact angle of the mercury where the interface touches the solid surface.
K is a conversion constant ($1.33 \times 10^{-4}$)
R the pore throat radius is in microns.

The mercury saturation is assumed to be equal to one minus the water saturation. Thus a scaling factor, F, to bring the mercury capillary pressure and other capillary pressure into agreement for any given water saturation can be calculated.

$$F = \frac{P_{Hg}}{P_{cp}} \bigg|_{S_w} \quad (2)$$

where Sw is the water saturation.

The capillary pressure ($P_{c-cp}$) of fresh-state sample is a function of the interfacial tension (interfacial energy) between the two phases used in the capillary pressure measurement and the contact angle of the two phases (see the aforementioned Anderson reference for explanation). The capillary pressure is defined as "Wettability Literature Survey—Part 4: Effects of Wettability on Capillary Pressure", *Journal of Petroleum Technology*, October 1987, pg. 1284, by William G. Anderson:

$$P_{cp} = (2\sigma_{cp}\cos\theta_{cp})/r \quad (3)$$

where:
r is the pore throat radius (assumed to be the radius of the capillary tube)
$\sigma_{cp}$ is the interfacial energy between the two phases used in the fresh state capillary pressure measurement (either oil/brine or gas/brine).
$\theta_{cp}$ is the contact angle, the angle of the water/oil/solid contact line or the water/gas/solid contact line.

Substituting equations (1) and (3) into equation (2) yields equation (4):

$$F = \frac{(2\,\sigma_{hg}\cos\theta_{hg})/r}{(2\,\sigma_{cp}\cos\theta_{cp})/r} \quad (4)$$

which can be reduced to $$F = (\sigma_{hg}\cos\theta_{hg})/(\sigma_{cp}\cos\theta_{cp}) \quad (5)$$

In the above expression only $\theta_{cp}$ depends on the rock wettability. The contact angle of the mercury ($\theta_{hg}$) is assumed to be 140° F. The surface tension of mercury ($\sigma_{hg}$) is taken as 480 dynes/cm. The interfacial tension of the oil and brine can be measured by standard means such as a tensiometer, the drop method, or other methods which can be found described in physical chemistry texts. Thus, wettability is a function of F which is determined from the comparison of mercury injection and capillary pressure measurements. F is determined at different water saturations and may vary with water saturation.

The mercury pressure can also be equated to a pore throat radius per equation (1). Thus F can also be determined as a function of pore throat radius.

The degree of wettability is identified from the determined cosine of the contact angle $\theta_{cp}$. The porous rock is identified as being wet with the first medium when the contact angle $\theta_{cp}$ extends from between 0° and 60° to about 75°. The porous rock is identified as being wet with the second medium when the contact angle $\theta_{cp}$ extends from between 105° and 120° to about 180°. The porous rock is identified as having mixed wettability of the first and second mediums when the contact angle $\theta_{cp}$ extends from about 75° to between 105° and 120° and, more particularly, neutrally wet at about 90°.

DESCRIPTION OF THE PREFERRED EMBODIMENT

In accordance with the present invention, the degree of wettability of porous rock of a core sample from a subterranean formation is quantitatively measured as an indication of the formation's potential for oil or gas production.

Figure 1:
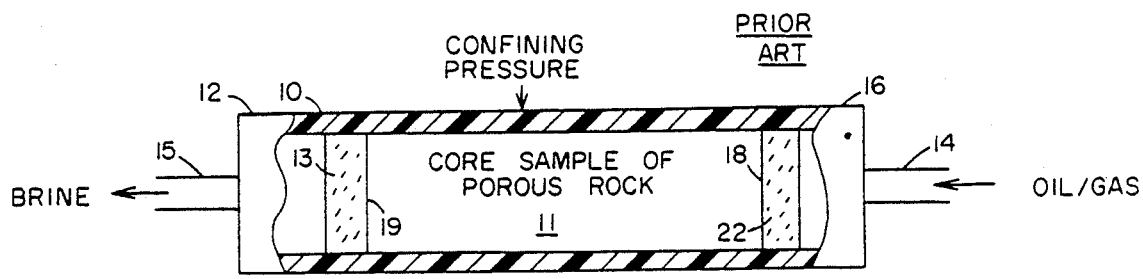
FIG. 1 illustrates prior art apparatus for carrying out fluid flow characteristic measurements on a core sample of a porous rock from a subterranean formation.

Apparatus that may be utilized in carrying out the method of the present invention is shown in FIG. 1 (prior art) and is more fully described in U.S. Pat. No. 4,924,187 to Sprunt et al., the teaching of which is incorporated herein by reference. Briefly, however, a pressure sleeve 10, preferably natural or synthetic rubber, surrounds a cylindrical core sample 11 of a porous rock to be measured for its fluid characteristics. Positioned between the core sample 11 and end 12 of the pressure sleeve 10 is a porous membrane 13, which is permeable to a first fluid saturating the core sample, but is impermeable to a second fluid used to displace the first fluid from the core sample. The second or displacing fluid is preferably an oil or gas which is immiscible with the first or saturating fluid which is preferably brine. The first saturating fluid is the wetting fluid for the porous membrane 13 which by way of example may be a ceramic plate or a membrane. Sleeve 10 is placed inside a suitable pressure vessel (not shown) that can be pressurized up to several thousand pounds per square inch. Typical of such pressure vessels are those described in U.S. Pat. Nos. 3,839,899 to McMillan; 4,688,238 to Sprunt et al., and 4,379,407 to Masse et al., the teachings of which are incorporated herein by reference. Through such a pressure vessel a confining pressure is applied to the sleeve 10 sufficient to seal, but not compress, the core sample. The pressure should force fluid to flow through the core sample and not along the surface of the core sample next to the sleeve. A fluid inlet 14 and a fluid outlet 15 feed into the ends 16 and 12 respectively of the sleeve 10.

Figure 2:
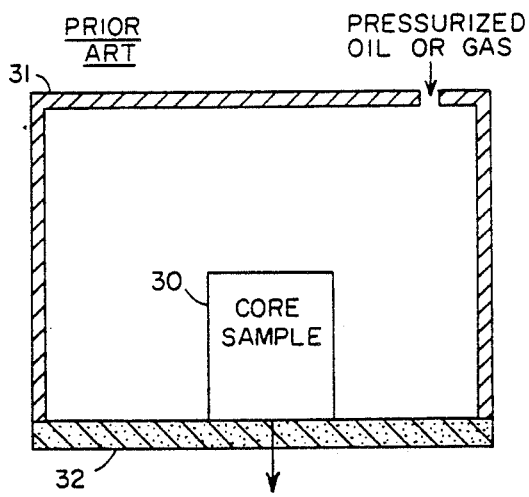
FIG. 2 illustrates prior art apparatus for carrying out capillary pressure measurements on a sample of porous rock.

Apparatus that may also be utilized in carrying out the method of the present invention is shown in FIG. 2 (prior art). Briefly, an unjacketed core sample 30 is placed in capillary contact with a porous member 32 within a closed cylinder 31 to hold oil or gas under pressure. Member 32 is permeable to a first fluid saturating the core sample, but is impermeable to the second fluid used to displace the first fluid from the core sample. The second or displacing fluid is preferably an oil or gas which is immiscible with the first or saturating fluid which is preferably brine. The first saturating fluid is the wetting fluid for the porous member 32 which by way of example may be a ceramic plate or membrane. Tissue paper and diatomaceous earth (not shown) is placed between the core sample 30 and the porous member 32 for capillary contact. Brine then moves in the direction of the arrow in FIG. 2 from the core sample 30 through the porous member 32.

Figure 3:
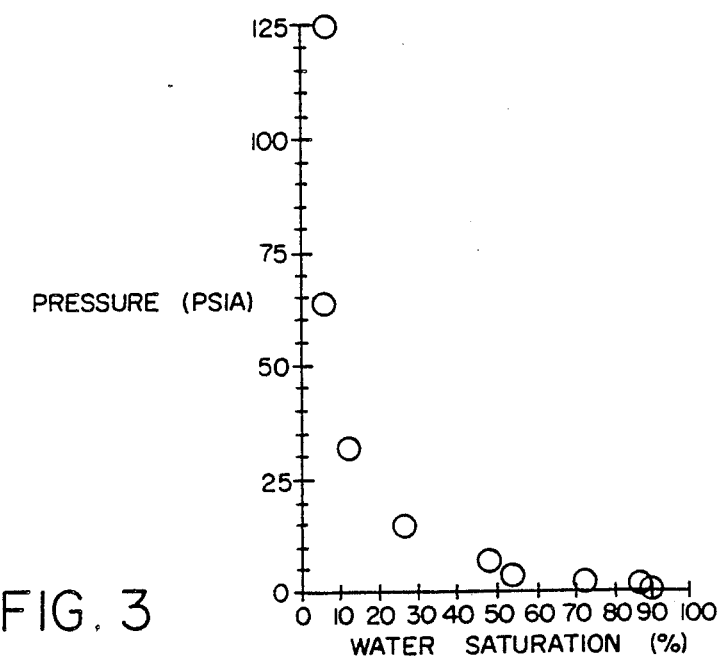
FIG. 3 illustrates a porous plate capillary pressure measurement for a core sample.

One fluid flow characteristic that can be measured with the apparatus of FIGS. 1 and 2 is the capillary pressure characteristic illustrated in FIG. 3 for a porous rock. Such capillary characteristic, as well as measurements thereof, is set forth in *Physical Principles of Oil Production*. McGraw Hill Book Company, 1949, pp. 304–311, by Morris Muskat. The importance of determining capillary characteristics pertains to the fluid distribution in a hydrocarbon-bearing (i.e., oil or gas) formation prior to its production. Capillary pressure is the pressure required to cause a fluid to displace from the openings (i.e., pores) in a porous rock another fluid with which it is not miscible and is dependant on the size of the openings, the interfacial tension between the two fluids, and the contact angle of the system.

While centrifuge techniques have been used for measurements of capillary pressure, corrections must be applied to such centrifuge measurements for the pressure gradient within the core sample. On the other hand, the porous plate measurement technique using the apparatus of FIG. 1 provides a direct measurement of capillary pressure curves (i.e., water saturation versus capillary pressure).

The relationship between capillary pressure P and the pore throat sizes connecting pores in the rock is expressed in U.S. Pat. No. 2,794,338 to Murphy et al., the teaching of which is incorporated by reference, in terms of a simple model which assumes that the pore throats are circular in cross section with radius R:

$$P = 2\sigma \cos\theta / R, \qquad (6)$$

where $\sigma$—interfacial tension between two immiscible phases in a porous rock, such as oil and brine or air and brine for examples, and $\theta$ = contact angle of the interface between the immiscible phases and the surface, measured relative to the wetting phase.

For a given rock sample, the pressure needed for the displacement of a wetting phase by a non-wetting phase depends on the pore throat sizes which limit the influx of the non-wetting phase and on the wettability of the pore surfaces. There is usually a range in pore throat sizes in rocks which is reflected in the pore volume filled and the pressure required to fill it.

For a two component immiscible fluid system like air-water, water is the wetting phase and air is the non-wetting phase on most sedimentary rock-forming mineral surfaces. When water completely wets a surface, the contact angle is zero and $\cos\theta = 1$. On the other hand, if pore surfaces are coated with organic materials derived from petroleum, like resins, asphaltenes, or the products of biological or thermal degradation, the water phase may not completely wet the surface making a contact angle with the surface between zero and 90 degrees. Nonpolar organic coatings on pore surfaces like paraffinic waxes can even render pore surfaces nonwettable by water so that the contact angle, between water and gas for example, is between 90 and 180 degrees. The sign of the cosine of the contact angle can therefore be used to determine whether a surface is hydrophylic (water wettable) or hydrophobic (water repellant). The magnitude of the cosine is a quantitative measure of the degree of wettability.

The pore surfaces in rocks are seldom perfectly flat so that, even if some type of microscopic measurement could be made, contact angles would be difficult to determine. An alternative solution is to make a measurement of wetting fluid displacement from an entire rock sample as a function of pressure applied to a displacing non-wetting phase. Since the composition and geometry of pore surfaces can vary greatly, even within a single rock sample, the contact angle $\theta$ deduced from a capillary pressure measurement on the whole sample should be regarded as an apparent contact angle, which is nevertheless indicative of the wettability.

Turning now to the method of the present invention, a quantitative measurement of wettability of a porous rock which does not depend on a direct measurement of contact angle is made by conducting two sequential capillary pressure measurements on the same core sample of porous rock. The first capillary pressure measurement is made by saturating the core sample with a medium like water or brine and displacing it with a phase medium like oil or air or gas. The second capillary pressure measurement is made by injecting non-wetting mercury under pressure into a core sample of the porous rock after evacuation. The mercury vapor, together with any residual gas present, corresponds to the wetting phase medium. Once the mercury pressure versus saturation curve is determined, it must be converted to an equivalent oil/brine or air/brine capillary pressure curve. The nonwetting phase saturation is equal to the mercury saturation. However, there is poor agreement as to what scaling factor should be used for the conversion because the scaling factor depends on lithology and wettability. The same scaling factor cannot be universally applied. In samples with mixed wettability, the same scaling factor may not be applicable over the entire pressure range because pressure is proportional to pore size and all pores may not have the same wettability. Thus the scaling factor is a measure of the wettability as a function of pore size.

The method requires that capillary pressure first be measured on a fresh core sample with wettability representative of the reservoir. Following the first capillary pressure measurement with either (i) oil and brine phases, (ii) gas and brine phases, or (iii) air and brine phases, the second capillary pressure measurement is made by mercury injection (i.e., mercury saturation versus mercury pressure). The mercury pressure $P_{hg}$ is translated to pore size radius R by the following:

$$R = 2\sigma_{hg}\cos\theta_{hg}/KP_{hg}, \quad (7)$$

where:
$\sigma_{hg}$ is the interfacial tension of the mercury,
$\theta_{hg}$ is the contact angle of the mercury where the interface touches the solid surface (assumed to be 140°), and
K is a conversion constant $(1.33 \times 10^{-4})$, therefore, R (microns) = $561/P_{hg}$(cm-Hg).

The scaling factor to bring the mercury and capillary pressure (on the fresh sample) into agreement for any given wetting phase saturation is calculated. This scaling factor F can be plotted against mercury pressure or pore throat size. If the capillary pressure has been measured for the core sample in both the fresh and cleaned, preferentially water-wet condition, the scaling factor in the two states can be compared.

The contact angle of oil/brine, gas/brine or air/brine and hence the wettability can be obtained from the scaling factor:

$$F = P_{hg}/P_{cp} \quad (8)$$

where:
$P_{hg}$ is the mercury injection pressure, and
$P_{cp}$ is the capillary pressure of the fresh sample. This capillary pressure may be either in an oil/brine measurement, in a gas/brine measurement, or in an air/brine measurement.

The capillary pressure ($P_{cp}$) of fresh-state sample is a function of the interfacial tension (interfacial energy) between the two phases used in the capillary pressure measurement and the contact angle of the two phases. The capillary pressure is defined as $$P_{cp} = (2\sigma_{cp}\cos\theta_{cp})/R \quad (9)$$

where:
R is the pore throat radius (assumed to be the radius of the capillary tube)
$\sigma_{cp}$ is the interfacial energy between the two phases used in the fresh state capillary pressure measurement (either oil/brine, gas/brine or air/brine).
$\theta_{cp}$ is the contact angle, the angle of water/oil/solid contact line or the water/gas/solid contact line. When $\theta_{cp}$ (oil/brine) is exactly 90° neither fluid preferentially wets the solids. When $\theta$ is between 0° and 60° to 75° the system is defined as water wet. When $\theta$ is between 180° and 105° to 120° the system is defined as oil-wet. In the middle range of contact angles the system is neutrally wet. Therefore:

$$F = P_{hg}/P_{cp} = (\sigma_{hg}\cos\theta_{hg})/(\sigma_{cp}\cos\theta_{cp}), \quad (10)$$

and rearranging for water wettability expressed as $\cos\theta_{cp}$:

$$\cos\theta_{cp} = \cos\theta_{hg}(\sigma_{hg}/\sigma_{cp})(P_{cp}/P_{hg}) \quad (11)$$

In the expression of equation (11) only $\theta_{cp}$ depends on the rock wettability. From the aforementioned Murphy et al. reference, the contact angle of the mercury ($\theta_{hg}$) is taken to be 140° and the surface tension of mercury ($\sigma_{hg}$) is taken as 480 dynes/cm. Other values of the contact angle of mercury may be used in special cases (see "The Contact Angle in Mercury Intrusion Porosimetry", Powder Technology, 29 (1981), pgs. 53–62, by Robert Good and Raouf Michail). The interfacial tension of the oil and brine can be measured by standard means such as a tensiometer, the drop method, or other methods which can be found described in physical chemistry texts. Thus, wettability is a function of F which is determined from the comparison of mercury injection and capillary pressure measurements.

Since F is a function of mercury pressure which can be equated to pore throat radius, the wettability of the rock can be measured as a function of pore throat radius. If wettability is known as a function of pore throat radius, it can be determined in mixed or neutral wettability rocks which pore throat sizes are water-wet or oil-wet.

Figure 4:
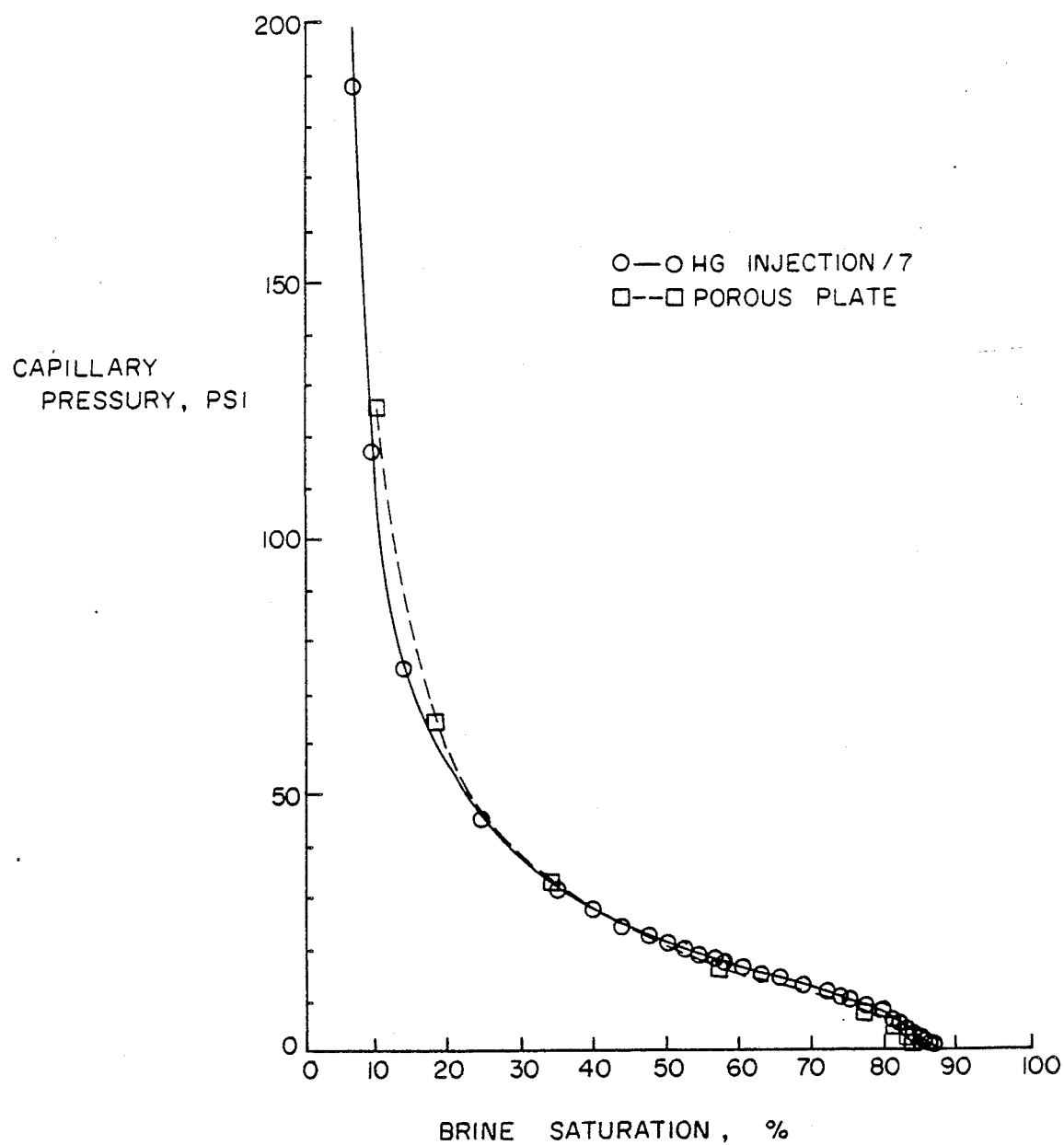
FIG. 4 illustrates an air-brine capillary pressure comparison of porous plate and mercury injection for a sandstone core sample with a uniform contact angle $\theta$.

FIG. 4 is an example of a sample which has pore surfaces which are only slightly water-wet. Both air-brine and mercury capillary pressure curves are illustrated. The same apparent contact angle results for all points along the air-brine capillary pressure curve.

Figure 5:
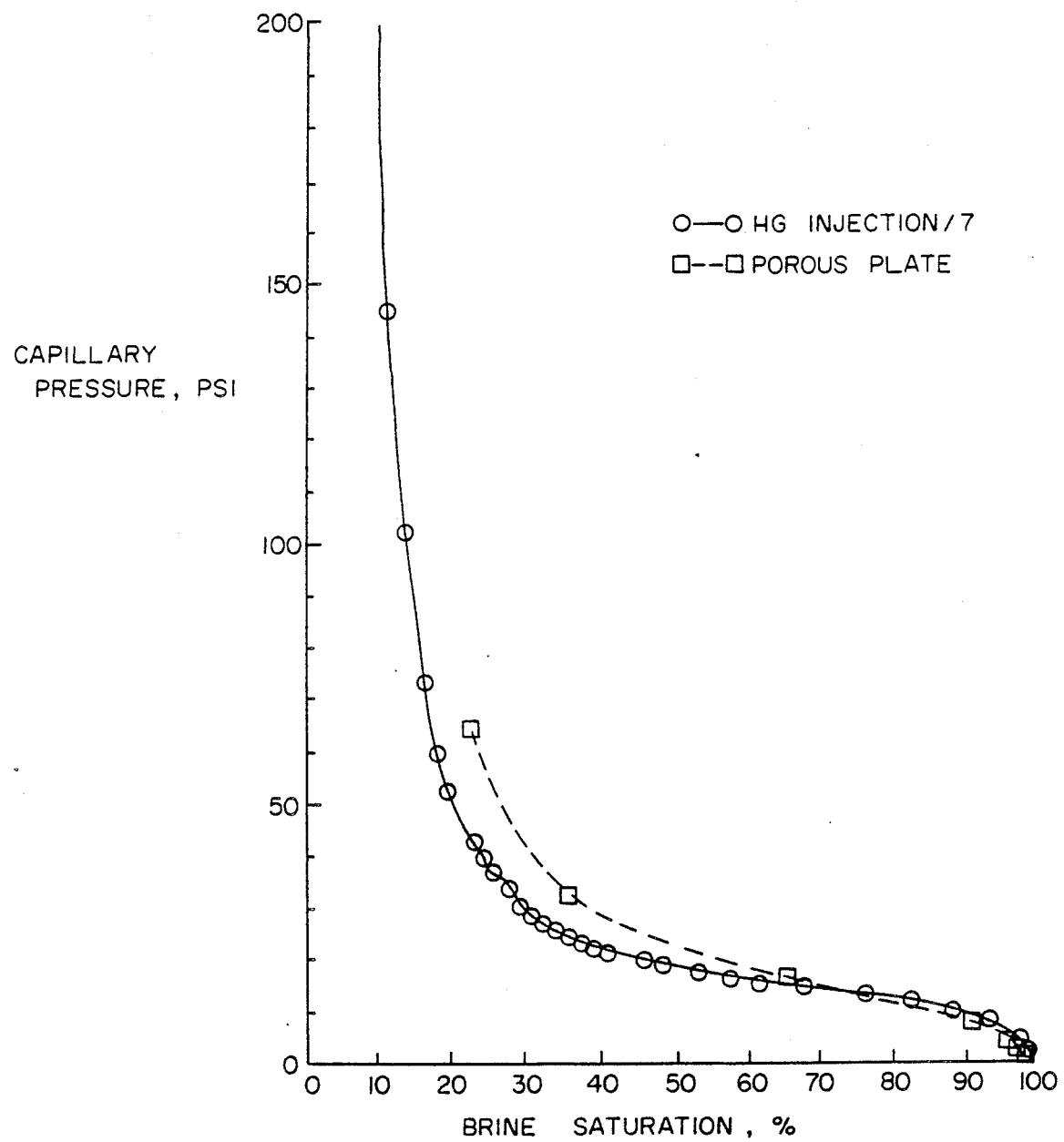
FIG. 5 illustrates an air-brine capillary pressure comparison of porous plate and mercury injection for a core sample of heterogeneous wettability.

Differences in wetting controlled by pore throat size can also be measured. Consider, for example, a reservoir which was initially water-wet and brine saturated. At a later time, nonwetting oil migrated into the reservoir displacing water from pores connected by the larger pore throats. The smaller pores, containing no oil, remained water-wet. The result is a mixed-wettability reservoir rock with larger pores having reduced water wettability and water-wet small pores. This type of heterogeneous wettability can be measured and quantified using sequential oil-brine followed by mercury capillary pressure curve measurements. FIG. 5 illustrates heterogeneous wettability of this type. In this illustration, the pores connected by the smaller throats are more water wet than the pores connected by larger throats.

It can therefore be seen from the foregoing that as the wettability of the pore surfaces change, changing the apparent contact angle $\theta$, the capillary pressure is changed accordingly. The drainage capillary pressure curve, measured for a two fluid phase system such as air-water or oil-water, can therefore be used as a quantitative measure of wettability for any part of a pore system when compared to the drainage capillary pressure curve for mercury on the same rock sample.

Having now described a preferred embodiment of the method of the present invention for measuring wettability of porous rock from a subterranean formation, it is to be understood that various modifications or changes may be made without departing from the spirit and scope of the invention as set forth in the appended claims.

We claim:

1. Method for measuring the wettability of a porous rock of a subterranean formation, comprising the steps of:
   a) measuring a first capillary pressure on said porous rock by saturating a sample of said porous rock having a wettability representative of the subterranean formation with a first medium phase and displacing said first medium with a second medium,
   b) measuring a second capillary pressure on said porous rock by injecting mercury into an evacuated sample of said porous rock, and
   c) determining wettability of said porous rock as a function of the ratio of said first and second capillary pressure measurements.

2. Method for measuring the wettability of a porous rock of a subterranean formation, comprising the steps of:
   a) saturating a core sample of said porous rock having a wettability representative of said subterranean formation with a first medium,
   b) displacing said first medium with a second medium that is immiscible with said first medium,
   c) measuring capillary pressure versus wetting phase saturation on said porous rock during the displacement of said first medium with said second medium in step b),
   d) injecting mercury into an evacuated core sample of said porous rock, said mercury acting as a non-wetting phase medium and mercury vapor acting as a wetting phase medium on said porous rock,
   e) measuring capillary pressure versus wetting phase saturation on said evacuated core sample during mercury injection of step d), and
   f) determining the ratio of said capillary pressure versus wetting phase saturation measurements of steps c) and e), and determining wettability from said ratio as a function of pore throat size.

3. Method for measuring the wettability of a porous rock of a subterranean formation, comprising the steps of:
   a) measuring a first capillary pressure versus wetting phase saturation by saturating a sample of said porous rock having a wettability representative of the subterranean formation with a first medium and displacing said first medium with a second that is immiscible with said first medium,
   b) measuring a second capillary pressure versus wetting phase saturation by injecting mercury into an evacuated sample of said porous rock, said mercury acting as a non-wetting phase and mercury vapor acting as a wetting phase, and
   c) determining interfacial tensions between said first and second mediums,
   d) identifying a value for the interfacial tension of injected mercury,
   d) identifying a value for the cosine of the contact angle of the injected mercury on a solid surface, and
   f) determining the wettability of said porous rock as a function of the cosine of the contact angle of the interface between the first and second mediums based on (i) the first and second capillary pressure versus wetting phase saturation measurements of steps a) and b), (ii) the determined interfacial tensions of steps c) and d), and (iii) the identified cosine of the mercury contact angle of step e).

4. Method for measuring the wettability of a porous rock, comprising the steps of:
   a) conducting a first capillary pressure measurement $P_{cp}$ on said porous rock by saturating a sample of said porous rock with a first medium and displacing said first medium with a second medium,
   b) determining the interfacial tension $\sigma_{cp}$ between said first and second mediums,
   c) conducting a second capillary pressure measurement $P_{hg}$ on said porous rock by injecting mercury into an evacuated sample of said porous rock,
   d) determining wettability of said porous rock as a function of the cosine of the contact angle $\theta_{cp}$ of the interface between said first and second mediums as follows:

$$\cos\theta_{cp} = \cos\theta_{hg}(\sigma_{hg}/\sigma_{cp})(P_{cp}/P_{hg})$$

where
   $\sigma_{hg}$ is the interfacial tension of said mercury,
   $\cos\theta_{hg}$ is the cosine of the contact angle $\theta_{hg}$ of the interface of said mercury on a solid surface.

5. The method of claim 4 wherein:
   a) said first capillary pressure measurement $P_{cp}$ is carried out by measuring capillary pressure versus the wetting-phase saturation of said porous rock with said first medium, and b) said second capillary pressure measurement $P_{hg}$ is carried out by measuring capillary pressure versus saturation of said porous rock with said mercury.

6. The method of claim 4 wherein an interfacial tension $\sigma_{hg}$ of 480 dynes per centimeter is utilized and said interfacial tension $\sigma_{cp}$ is determined from interfacial tension measurements.

7. The method of claim 4 wherein a contact angle $\theta_{hg}$ of about 140° is utilized.

8. The method of claim 4 further comprising the step of identifying said porous rock as being wet with said first medium when the contact angle $\theta_{cp}$ extends from between 0° and 60° to about 75°.

9. The method of claim 4 further comprising the step of identifying said porous rock as being wet with said second medium when the contact angle $\theta_{cp}$ extends from between 105° and 120° to about 180°.

10. The method of claim 4 further comprising the step of identifying said porous rock as having mixed wettability of said first and second mediums when the contact angle $\theta_{cp}$ extends from about 75° to between 105° and 120°.

11. The method of claim 4 further comprising the step of identifying said porous rock as being equally wet with both said first and second mediums when the contact angle $\theta_{cp}$ is approximately 90°.

* * * * *